United States Patent
Cheng

(10) Patent No.: US 9,486,365 B2
(45) Date of Patent: Nov. 8, 2016

(54) EARPLUG AND ELECTRONIC DEVICE USING THE SAME

(71) Applicant: Chiun Mai Communication Systems, Inc., New Taipei (TW)

(72) Inventor: Chuan-Hsien Cheng, New Taipei (TW)

(73) Assignee: Chiun Mai Communication Systems, Inc., New Taipei (TW)

( * ) Notice: Subject to any disclaimer, the term of this patent is extended or adjusted under 35 U.S.C. 154(b) by 329 days.

(21) Appl. No.: 14/195,858

(22) Filed: Mar. 4, 2014

(65) Prior Publication Data
US 2015/0136148 A1    May 21, 2015

(30) Foreign Application Priority Data
Nov. 18, 2013   (CN) .......................... 2013 1 0575960

(51) Int. Cl.
*A61F 11/00*    (2006.01)
*A61F 11/08*    (2006.01)
*H04R 1/10*    (2006.01)
*H04R 1/28*    (2006.01)

(52) U.S. Cl.
CPC ............. *A61F 11/08* (2013.01); *H04R 1/1016* (2013.01); *A61F 2011/085* (2013.01); *H04R 1/2811* (2013.01); *H04R 2499/11* (2013.01)

(58) Field of Classification Search
CPC .. A61F 11/08; A61F 2011/085; A61F 11/14; A61F 11/12; A61F 11/00; A61F 13/00008; A61F 13/00034; A61F 13/00063; A61F 13/00068; A61F 13/041; A61F 13/10; A61F 13/141; A61F 13/2005; A61F 13/2017; A61F 2013/00174; A61F 2013/00246; H04R 1/1016; H04R 1/2811; H04R 2499/11; H04R 2460/11; G01N 2291/02491; G01N 2291/0421; G10K 11/16; B29C 44/1271; C08G 2101/0008; C08J 2205/05; C08J 2375/04; C08J 2421/00; C08J 9/0061
USPC ................................... 128/864–868; 181/135
See application file for complete search history.

(56) References Cited

U.S. PATENT DOCUMENTS

| | | | |
|---|---|---|---|
| 6,148,821 A * | 11/2000 | Falco ...................... | A61F 11/08 128/864 |
| 8,343,397 B2 * | 1/2013 | Woo ........................ | A61F 11/08 264/275 |
| 2009/0038625 A1 * | 2/2009 | Cortez ................... | A61F 11/08 128/864 |
| 2010/0275931 A1 * | 11/2010 | Seyed ..................... | A61F 11/08 128/864 |

* cited by examiner

*Primary Examiner* — Michael Brown
(74) *Attorney, Agent, or Firm* — Zhigang Ma

(57) ABSTRACT

An earplug includes a sleeve, a resonance tube, and a tip. The sleeve has a plurality of slits, and the resonance tube is connected between the sleeve and the tip. When the sleeve is pressed to deform, the slits are opened to allow sound to enter the sleeve, and pass through the resonance tube and the tip.

8 Claims, 4 Drawing Sheets

EARPLUG AND ELECTRONIC DEVICE USING THE SAME

BACKGROUND

1. Technical Field

The present disclosure generally relates to earplugs, and particularly, to an earplug for use in an electronic device.

2. Description of Related Art

Earplug is often inserted in the ear canal to protect hearing. However, when users need to receive a telephone call, the earplug has to be taken out first. It can be inconvenient for users.

Therefore, there is a room for improvement within the art.

BRIEF DESCRIPTION OF THE DRAWINGS

Many aspects of the earplug and electronic device using the same can be better understood with reference to the following drawings. The components in the drawings are not necessarily to scale, the emphasis instead being placed upon clearly illustrating the earplug and electronic device using the same. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean "at least one."

Figure 1:
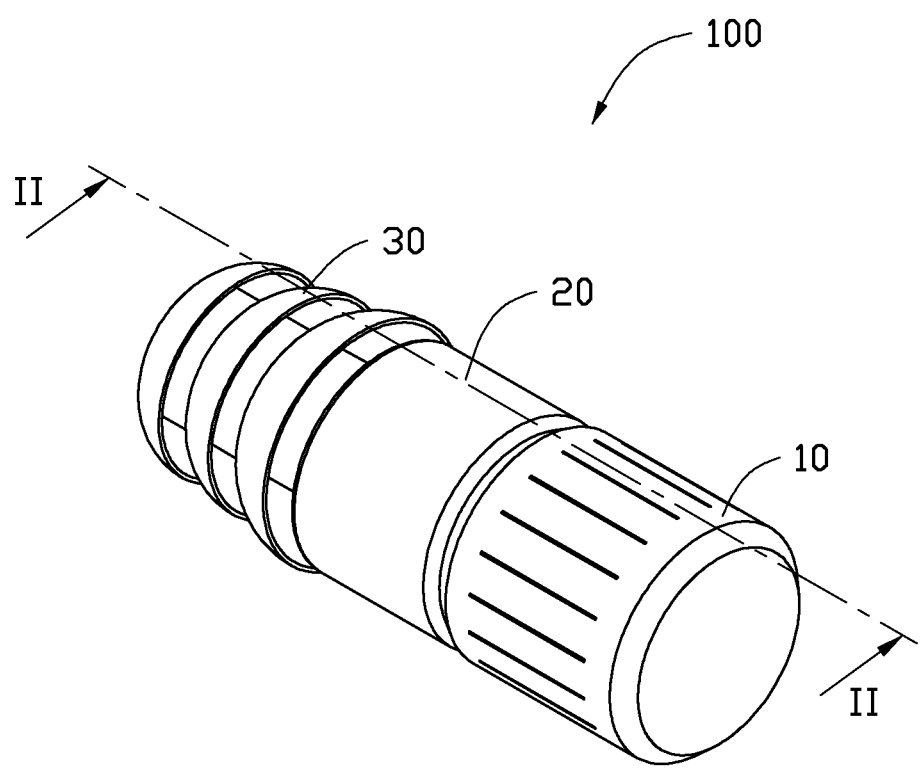
FIG. 1 is an isometric view of an earplug according to one embodiment.
Figure 2:
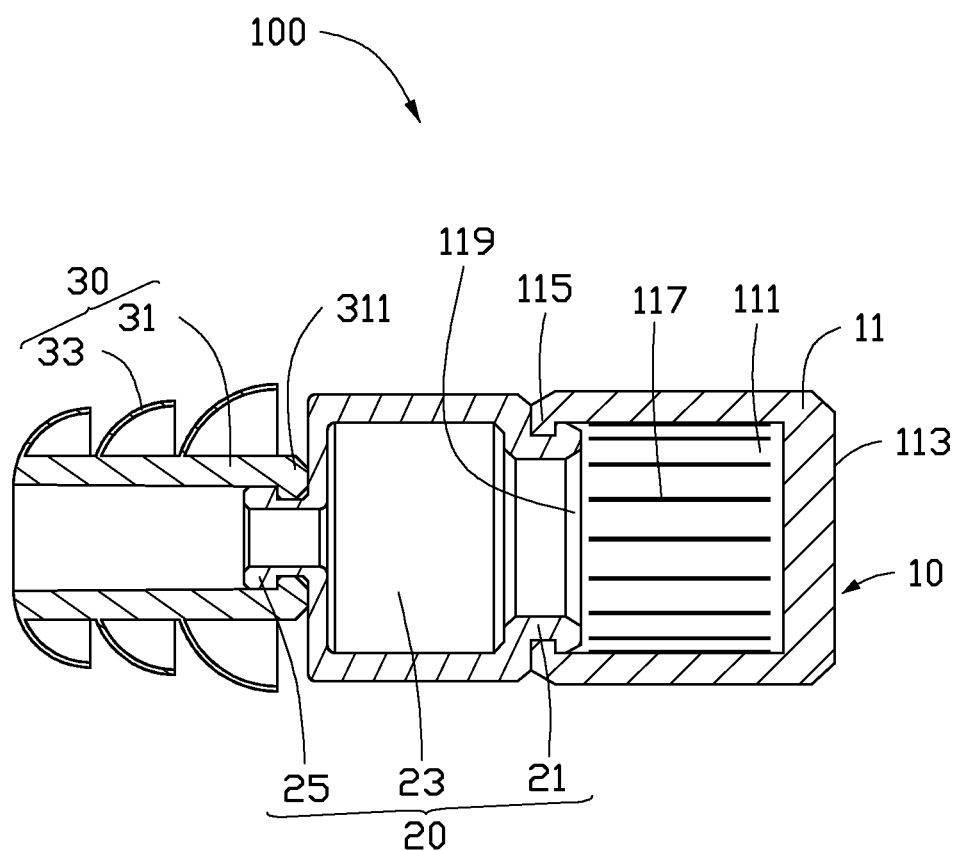
FIG. 2 is a cross-sectional view of FIG. 1 taken along line II-II.
Figure 3:
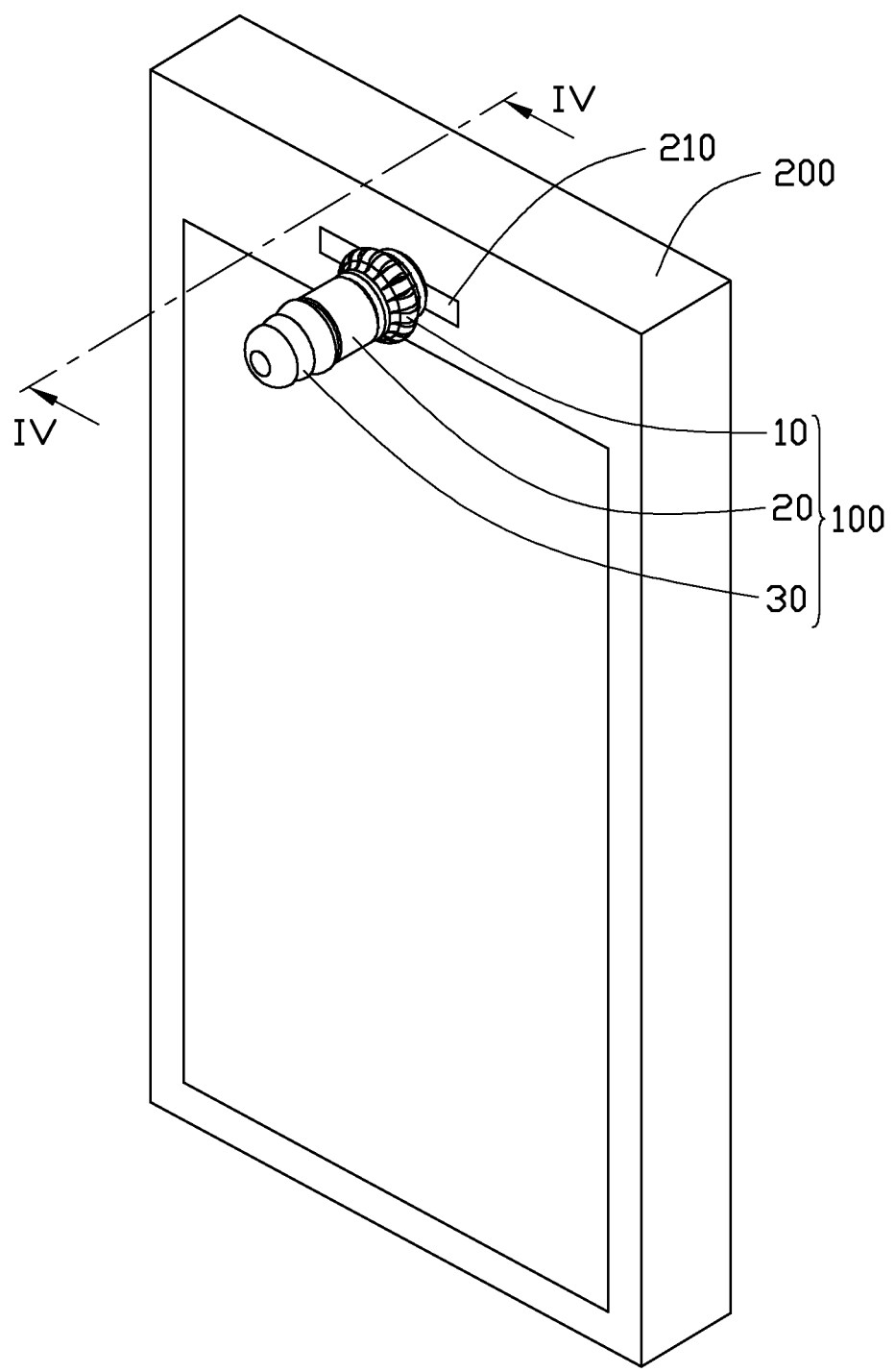
FIG. 3 is an isometric view of the earplug of FIG. 1 assembled to an electronic device.
Figure 4:
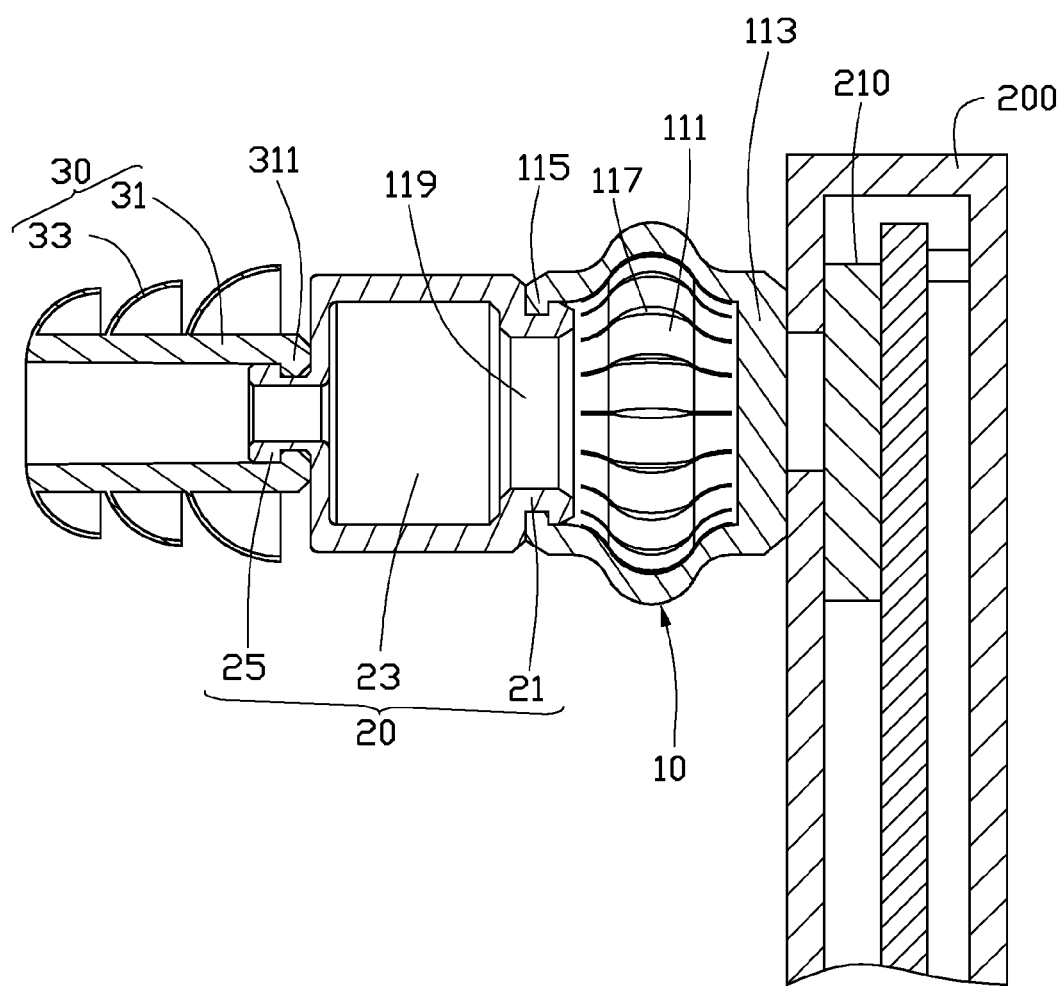
FIG. 4 is a cross-sectional view of FIG. 3 taken along line IV-IV.

FIGS. 1 and 2 show an earplug 100 according to an exemplary embodiment. FIGS. 3 and 4 show that the earplug 100 can be installed on a speaker 210 of an electronic device 200, such as a mobile phone or a computer. The earplug 100 includes a sleeve 10, a resonance tube 20, and a tip 30. The resonance tube 20 is connected between the sleeve 10 and the tip 30.

FIG. 2 shows that the sleeve 10 is made of elastic material, and is a hollow structure. The sleeve 10 has a first end 113 and an opposite second end 115. The first end 113 is configured for abutting against the speaker 210 of the electronic device 200, and the second end 15 is configured for latching with the resonance tube 20. The sleeve 10 includes a peripheral wall 11 surrounding a cavity 111. The peripheral wall 11 defines a plurality of slits 117 along an axial direction of the sleeve 10. The slits 117 remain closed in a natural state. Outside sound is muted through the slits 117. When the sleeve 10 is manually deformed, the slits 117 are opened allowing outside sound to enter the cavity 111. The second end 115 defines an opening 119 communicating with the cavity 111.

The resonance tube 20 includes a first latching end 21, a resonant cavity 22, and a second latching end 25. The first latching end 21 and the second latching end 25 are positioned at opposite sides of the resonant cavity 22. The first latching end 21 is used for latching with the second end 115 of the sleeve 10. The resonant cavity 22 communicates with the opening 119, and can produce resonance for increasing volume. In this exemplary embodiment, the resonant cavity 22 is a single cavity. In other embodiments, the resonant cavity 22 may be made of a plurality of cavities. The size of the second latching end 25 is smaller than the first latching end 21.

The tip 30 includes a central pipe 31 and a plurality of domed flanges 33 positioned around the central pipe 31. The central pipe 31 has opposite opening ends allowing sound from the resonance tube 20 to enter the ear canal. One of the opening ends of the central pipe 31 has a hooked portion 311. The hooked portion 311 is latched with the second latching end 25 for fixing the tip 30 on the resonance tube 20. The domed flanges 33 are made from silicone rubber, and are spaced from each other. The size of the domed flanges 33 are gradually increasing toward the resonance tube 20. The domed flanges 33 conform to the shape of the ear canal forming a seal for preventing loud noises from entering the ear canal.

In assembly, the first latching end 21 is latched with the second end 115 of the sleeve 10, and the hooked portion 311 is latched with the second latching end 25 fixing the sleeve 10, the resonance tube 20, and the tip 30 together. The resonant cavity 22 communicates with the cavity 111 and the central pipe 31.

In use, the tip 30 is inserted in the ear canal, and the sleeve 10 is exposed from the ear canal. Since the slits 117 are at a closed state and the domed flanges 33 seal the ear canal, hearing is effectively protected from loud noises. FIGS. 3 and 4 show that when user needs to receive a call, the speaker 210 of the electronic device 200 is manually held near the ear, abutting the speaker 210 of the electronic device 200 against the first end 113 of the earplug 100 in the ear canal. The sleeve 10 of the earplug 100 is forced to deform to open the slits 117. The sound from the speaker 210 enters the cavity 111 and the resonant cavity 22 from the slits 117. The resonant cavity 22 produces resonance for increasing the sound, and the sound from the resonance tube 20 enters the ear canal through the central pipe 31. The earplug does not need to be removed from the ear canal when a call is received.

In other alternative embodiments, the earplug 100 may be attached to the speaker 210 of the electronic device 200. When user needs to receive a call, the sleeve 10 is manually deformed to open the slits 117. Then, the earplug 100 is put into the ear canal for receiving the call.

It is to be understood, however, that even through numerous characteristics and advantages of the present disclosure have been set forth in the foregoing description, together with details of the structure and function of the disclosure, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. An earplug comprising:
   a sleeve comprising a plurality of slits;
   a resonance tube; and
   a tip, the resonance tube connected between the sleeve and the tip;
   wherein when the sleeve is pressed to deform, the slits are opened to allow sound to enter the sleeve, and pass through the resonance tube and the tip; and wherein the resonance tube includes a first latching end, a resonant cavity, and a second latching end, the first latching end and the second latching end are positioned at opposite sides of the resonant cavity, and the first latching end is latched with the sleeve.

2. The earplug as claimed in claim 1, wherein the sleeve includes a peripheral wall surrounding a cavity, the peripheral wall defines the slits along an axial direction of the sleeve.

3. The earplug as claimed in claim 1, wherein the size of the second latching end is smaller than the first latching end.

4. The earplug as claimed in claim 3, wherein the tip includes a central pipe and a plurality of domed flanges positioned around the central pipe, and the central pipe has opposite opening ends for allowing sound from the resonance tube to enter user's ear canal.

5. The earplug as claimed in claim 4, wherein the domed flanges are made from silicone rubber, and are spaced from each other, the size of the domed flanges are gradually increased toward the resonance tube.

6. An electronic device, comprising:
a speaker; and
an earplug attached to the speaker, the earplug comprising:
   a sleeve comprising a plurality of slits;
   a resonance tube; and
   a tip, the resonance tube connected between the sleeve and the tip;
wherein when the sleeve is pressed to deform, the slits are opened to allow sound to enter the sleeve, and pass through the resonance tube and the tip.

7. The electronic device as claimed in claim 6, wherein the tip includes a central pipe and a plurality of domed flanges positioned around the central pipe, the central pipe has opposite opening ends for allowing sound from the resonance tube to enter user's ear canal.

8. The electronic device as claimed in claim 7, wherein the domed flanges are made from silicone rubber, and are spaced from each other, the size of the domed flanges are gradually increased toward the resonance tube.

* * * * *